US00PP27167P3

(12) United States Plant Patent
Zaiger et al.

(10) Patent No.: US PP27,167 P3
(45) Date of Patent: Sep. 20, 2016

(54) PEACH TREE NAMED 'KRISTA'

(50) Latin Name: *Prunus persica*
Varietal Denomination: Krista

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 119 days.

(21) Appl. No.: 14/544,289

(22) Filed: Dec. 22, 2014

(65) Prior Publication Data

US 2016/0183423 P1 Jun. 23, 2016

(51) Int. Cl.
*A01H 5/08* (2006.01)

(52) U.S. Cl.
USPC ..... Plt./197

(58) Field of Classification Search
USPC ..... Plt./197
See application file for complete search history.

*Primary Examiner* — Anne Grunberg

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright growth of tree.
2. Regular and productive bearer of large size fruit.
3. Fruit with an attractive dark red skin color.
4. Fruit with firm, yellow flesh.
5. Fruit with good flavor and eating quality.

1 Drawing Sheet

Botanical designation: *Prunus persica.*
Variety denomination: 'Krista'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach and nectarine trees, which are known to us, and mentioned herein, 'Super Lady' Peach (U.S. Plant Pat. No. 15,578), 'Super Zee' Peach (U.S. Plant Pat. No. 17,874), the proprietary non-patented peach selections '54ZH822', '170LX160', '37ZD298', '196LT268' and '211LK116'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. from a first generation cross between the proprietary non-patented peach selections with the field identification numbers '54ZH822' and '170LX160'. The seed parent (54ZH822) peach non-patented originated from a cross between our proprietary non-patented peach selection '37ZD298' and 'Super Lady' Peach (U.S. Plant Pat. No. 15,578). The non-patented peach pollen parent (170LX160) originated from a cross between our proprietary non-patented peach selections '196LT268' and '211LK116'. A large number of these first generation peach seedlings were planted and maintained on their own root systems, during which time we recognized the desirable tree and fruit characteristics of the present seedling and selected it in 2011 for additional asexual propagation and commercialization.

ASEXUAL REPRODUCTION OF THE VARIETY

In 2011 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of peach tree (*Prunus persica*) is of large size, vigorous, upright growth and a regular and productive bearer of large, yellow flesh, clingstone fruit with good flavor and eating quality. The fruit is further characterized by having an attractive dark red skin color and having good handling and shipping quality. In comparison to its non-patented proprietary peach seed parent '54ZH822' the fruit of the new variety is larger in size and is approximately 17 days earlier in maturity. In comparison to its non-patented proprietary peach pollen parent '170LX160' the fruit of the new variety is larger in size and is approximately 32 days earlier in maturity. In comparison to its ancestor 'Super Lady' Peach (U.S. Plant Pat. No. 15,578) the fruit of the new variety is larger in size. In comparison to the commercial variety 'Super Zee' Peach (U.S. Plant Pat. No. 17,874) the fruit of the new variety is larger in size and is approximately 8 days later in maturity.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 3 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 3 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies slightly with soil type, fertility of soil and climatic conditions.

*Form*.—Upright, usually pruned to vase shape.

*Branching habit*.—Upright, crotch angle approximately 35°, increases with heavy crop load.

*Productivity*.—Productive, thinning and spacing of fruit necessary for desired marketable size. Fruit set varies with climatic conditions during bloom time.

*Bearer*.—Regular, has had adequate fruit set 2 consecutive years. No alternate bearing observed.

*Fertility*.—Self-fertile.

*Density*.—Medium dense, pruning to vase shape desirable for sunlight penetration to center of tree to enhance fruit color and health of fruit wood.

*Hardiness*.—Hardy in all stone fruit growing areas of California. Tree grown in USDA Hardiness Zone 9. Winter chilling requirement approximately 500 hours at or below 45° F.

Trunk:

*Size*.—Large. Average circumference 40.7 cm at 22.9 cm above ground on a 3 year old tree.

*Stocky*.—Medium stocky.

*Texture*.—Medium shaggy, roughness increases with age.

*Color*.—Varies from 10YR 3/2 to 2.5Y 4/2.

Branches:

*Size*.—Medium. Average circumference 12.7 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 28 in a 25.8 square cm area. Average length 4.0 mm. Average width 1.8 mm. Color varies from 10YR 6/10 to 10YR 5/8.

*Color*.—New growth varies from 5GY 6/6 to 5GY 5/6. Mature growth varies from 10YR 3/4 to 2.5Y 3/4, varies with age of growth.

Leaves:

*Size*.—Large. Average length 166.6 mm. Average width 48.8 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentation over midrib and leaf veins. Lower surface relatively smooth, except for small ridges created by midrib and pinnate venation. Both upper and lower surfaces glabrous.

*Petiole*.—Average length 11.3 mm. Average width 2.0 mm. Longitudinally grooved. Surface — glabrous. Color varies from 5GY 5/8 to 5GY 4/8.

*Glands*.—Type — reniform. Size — large. Average length 1.7 mm. Average diameter 1.1 mm. Number varies from 3 to 6, average number 4. Located primarily on the base of the leaf blade and the upper portion of the petiole. Color varies from 2.5GY 6/6 to 5GY 6/6.

*Stipules*.—Average number 2. Average length 12.5 mm. Edges — pectinate. Color varies from 5GY 6/6 to 5GY 5/8.

*Color*.—Upper surface varies from 5GY 4/4 to 5GY 3/6. Lower surface varies from 5GY 4/4 to 5GY 4/6. Midvein color varies from 2.5GY 7/8 to 5GY 7/8.

Flower buds:

*Size*.—Large. Average length 20.0 mm. Average diameter 10.2 mm.

*Hardiness*.—Hardy with respect to California winters.

*Density*.—Medium dense.

*Form*.—Conical, becoming elongated just before opening.

*Pedicel*.—Average length 3.8 mm. Average width 1.3 mm. Color varies from 2.5GY 6/6 to 5GY 6/6. Surface — glabrous.

*Color*.—Varies from 5RP 8/6 to 5RP 7/10.

Flowers:

*Blooming period*.—Date of First Bloom Feb. 6, 2014. Date of Petal Fall Feb. 16, 2014, varies slightly with climatic conditions.

*Size*.—Large, showy. Average height 20.4 mm. Average diameter 41.8 mm.

*Petals*.—Normally 5, alternately arranged to sepals. Petal apex — rounded. Petal base — acuminate. Size — large. Average length 19.6 mm. Average width 18.3 mm. Form — orbicular. Arrangement — overlapping. Margin — sinuate. Color varies from 5RP 8/4 to 5RP 8/6, fades with age of flower.

*Sepals*.—Normally 5, alternately arranged to petals. Size — large. Average length 5.6 mm. Average width 5.5 mm. Shape — ovate. Apex — rounded to triangular. Margin — entire. Upper surface glabrous, lower surface pubescent. Color — upper surface varies from 5GY 5/6 to 2.5R 3/6. Lower surface varies from 2.5R 2/4 to 5R 2/4.

*Stamens*.—Average number per flower 45. Average filament length 15.0 mm. On average, the stamens are above the height of the petals. Filament color N 9.5/(white). Anther color varies from 7.5R 4/12 to 5Y 8/8.

*Pollen*.—Self fertile. Color varies from 2.5Y 7/12 to 5Y 7/12.

*Pistil*.—Number — normally one. Average length 15.1 mm. Position of stigma an average of 2.6 mm below anthers. Surface — pubescent. Color varies from 10Y 8/6 to 10Y 7/6.

*Fragrance*.—Moderate.

*Color*.—Varies from 5RP 8/4 to 7.5RP 8/4.

*Pedicel*.—Average length 3.8 mm. Average width 1.4 mm. Color varies from 2.5GY 6/8 to 5GY 6/6. Surface glabrous.

*Number flowers per flower bud*.—Normally one.

Fruit:

*Maturity when described*.—Firm ripe and ready for consumption.

*Date of first picking*.—May 3, 2014.

*Date of last picking*.—May 13, 2014, varies slightly with climatic conditions.

*Size*.—Large. Average diameter axially 61.9 mm. Average transversely in suture plane 72.8 mm. Average weight 201.6 grams, varies slightly with fertility of the soil, amount of thinning and climatic conditions.

*Form*.—Globose.

*Suture*.—Slightly lipped.

*Ventral surface*.—Very slightly lipped.

*Apex*.—Retuse.

*Base*.—Retuse.

*Stem cavity*.—Rounded to slightly elongated in suture plane. Average depth 7.6 mm. Average diameter 7.4 mm.

Stem:

*Size*.—Medium. Average length 7.4 mm. Average diameter 3.8 mm.

*Color*.—Varies from 2.5GY 5/8 to 5GY 5/8.

Flesh:

*Ripens*.—Evenly.

*Texture*.—Firm, meaty, crisp.

*Fibers*.—Few, small, tender.

*Firmness*.—Firm, comparable to other commercial varieties.

*Aroma*.—Heavy.

*Amydgalin*.—Undetected.

*Eating quality*.—Good.

*Flavor*.—Good.

*Juice*.—Moderate amount, enhances flavor.

*Acidity*.—Not available.

*Brix*.—Average Brix 9.9°, varies slightly with amount of fruit per tree and climatic conditions.

*Color*.—Varies from 2.5Y 8/6 to 5R 5/8.

*Pit cavity*.—Average length 33.0 mm. Average width 26.0 mm. Average depth 14.0 mm. Color varies from 5Y 7/8 to 2.5Y 7/10.

Skin:

*Thickness*.—Medium.

*Surface*.—Smooth.

*Pubescence*.—Moderate amount, short in length.

*Tendency to crack*.—None.

*Color*.—Ground color varies from 7.5YR 6/8 to 5YR 6/8. Overspread with 7.5R 3/6 to 5R 3/8.

*Tenacity*.—Tenacious to flesh.

*Astringency*.—Undetected.

Stone:

*Type*.—Clingstone, strong adherence to flesh.

*Size*.—Medium to large. Average length 32.0 mm. Average width 25.0 mm. Average thickness 24.0 mm.

*Form*.—Ovoid.

*Base*.—Flat.

*Apex*.—Pointed. Average length 0.7 mm.

*Surface*.—Pitted throughout, pits vary from round to elongated.

*Sides*.—Unequal, one side extending further from suture plane.

*Ridges*.—Small, narrow ridge extending from base toward apex.

*Tendency to split*.—Slight to none.

*Color*.—Varies from 10YR 7/6 to 2.5Y 8/6 when dry.

Kernel:

*Size*.—Medium. Average length. 15.5 mm. Average width 10.7 mm. Average depth 6.7 mm.

*Form*.—Ovoid.

*Viability*.—Non-viable, incomplete embryo development.

*Skin color*.—Varies from 5Y 9/4 to 5Y 8.5/4.

Use: Dessert.

*Market*.—Local and long distance.

Keeping quality: Good, held firm in cold storage for 3 weeks at 38° to 42° F. without internal breakdown or appreciable loss of flavor.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree, (*Prunus persica*) substantially as illustrated and described.

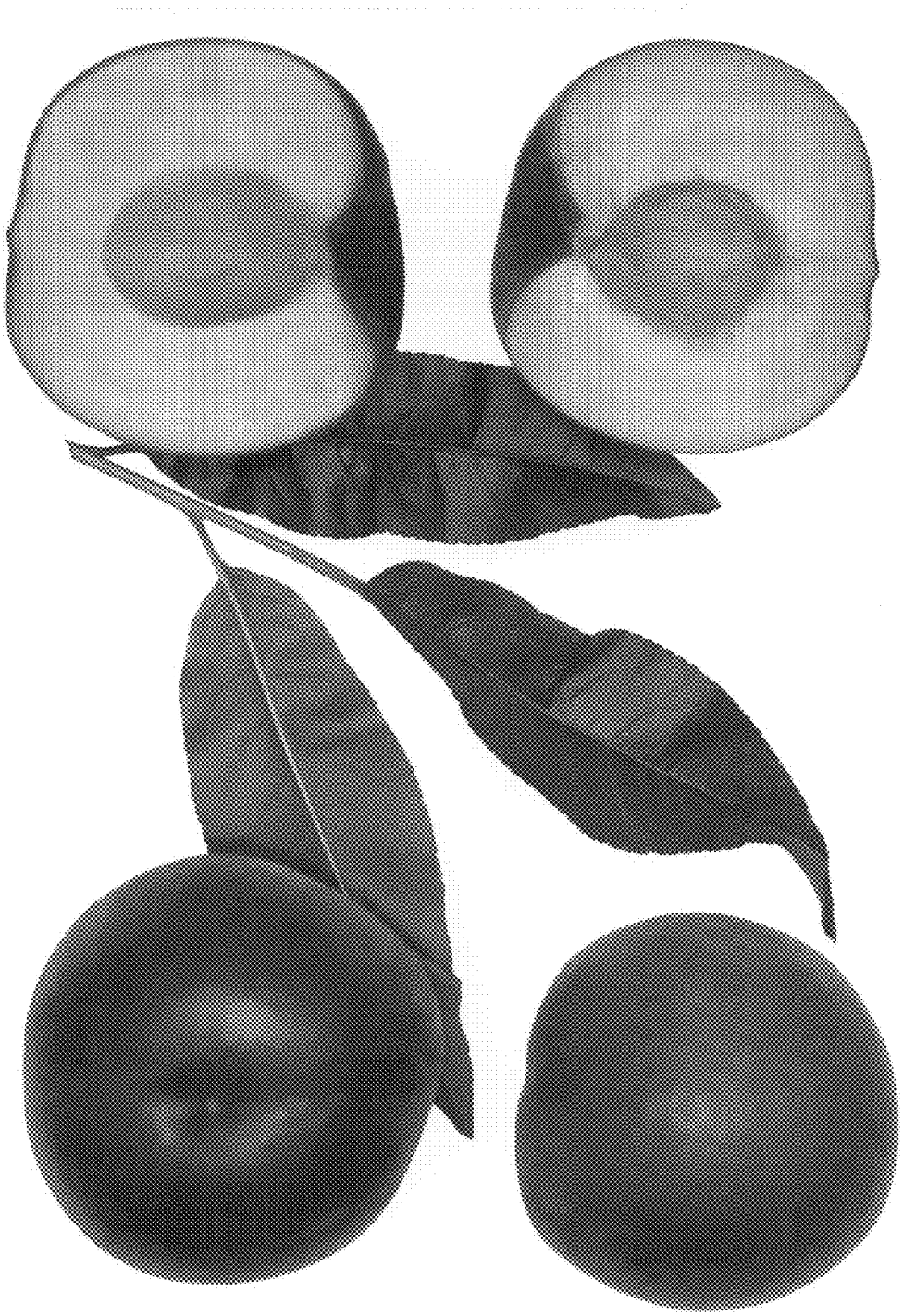

* * * * *